(12) United States Patent
Heiliger et al.

(10) Patent No.: US 6,528,462 B1
(45) Date of Patent: Mar. 4, 2003

(54) PROCESS FOR INHIBITING THE EMISSION OF HYDROGEN SULFIDE AND/OR MERCAPTANS FROM SULFURIZED ORGANIC COMPOUNDS

(75) Inventors: Ludger Heiliger, Neustadt/Weinstr.; Alfred Pauli, Reilingen; Joachim Hegmann, Limburgerhof; Michael Wühr, Hirschberg; Achim Fessenbecker, Waghäusel-Kirrlach; Kurt Schilling, Schwetzingen, all of (DE)

(73) Assignee: Rhein Chemie Rheinau GmbH, Mannheim (DE)

( * ) Notice: Subject to any disclaimer, the term of this patent is extended or adjusted under 35 U.S.C. 154(b) by 159 days.

(21) Appl. No.: 09/621,726

(22) Filed: Jul. 24, 2000

(30) Foreign Application Priority Data

Jul. 29, 1999 (DE) .......................... 199 35 672

(51) Int. Cl.[7] .......................... C10M 135/02
(52) U.S. Cl. .......................... 508/322; 568/18
(58) Field of Search .......................... 508/322; 568/18

(56) References Cited

U.S. PATENT DOCUMENTS

| | | | | |
|---|---|---|---|---|
| 4,070,295 A | * | 1/1978 | Miller | 252/48.6 |
| 4,207,195 A | * | 6/1980 | Horodysky | 252/46.6 |
| 4,778,609 A | | 10/1988 | Koch et al. | 252/32.5 |
| 4,834,775 A | * | 5/1989 | Rodriguez et al. | 44/51 |
| 4,873,006 A | | 10/1989 | Vinci et al. | 252/47.5 |
| 4,904,402 A | * | 2/1990 | Audeh | 252/46.3 |
| 4,994,090 A | * | 2/1991 | Rodriguez et al. | 44/301 |
| 5,028,340 A | * | 7/1991 | Gallup | 210/753 |
| 5,062,976 A | * | 11/1991 | Audeh | 252/45 |
| 5,284,497 A | * | 2/1994 | Egiebor et al. | 44/561 |
| 5,368,617 A | * | 11/1994 | Kindig | 44/622 |
| 5,505,746 A | * | 4/1996 | Chriswell et al. | 44/624 |

OTHER PUBLICATIONS

Ullmanns Encyclopedia of Industrial Chemistry, vol. A26, pp. 775–776, revised edition, (month unavailable) 1995, Thiols and Organic Sulfides.

Houben–Weyl, Methoden der organisch Chemie, vol. E11/part 1, pp. 136–137, (date unavailable) Gundermann et al, Disulfane.

* cited by examiner

*Primary Examiner*—Ellen M. McAvoy
(74) *Attorney, Agent, or Firm*—Joseph C. Gil; Noland J. Cheung; Jennifer R. Seng

(57) ABSTRACT

The present invention provides a process for inhibiting the emission of hydrogen sulfide and/or mercaptans from sulfurized organic compounds, which generally contain a high proportion of sulfur by treating the sulfurized organic compounds with organic hydroperoxides.

3 Claims, No Drawings

PROCESS FOR INHIBITING THE EMISSION OF HYDROGEN SULFIDE AND/OR MERCAPTANS FROM SULFURIZED ORGANIC COMPOUNDS

FIELD OF THE INVENTION

The present invention provides a process for inhibiting the emission of hydrogen sulfide and/or mercaptans from sulfurized organic compounds which normally contain a high proportion of sulfur.

BACKGROUND OF THE INVENTION

It is known that sulfur-containing organic compounds which contain a high proportion of sulfur and are used as so-called "sulfur carriers", readily tend to emit hydrogen sulfide and/or mercaptans when used, for example, as (EP additives) in lubricants, in particular when these sulfur-containing lubricants are subjected to elevated temperatures and stresses during use.

One of the many requirements placed on these sulfur-containing compounds is that, if possible, no emissions of hydrogen sulfide and/or mercaptans should occur since these compounds not only cause a nuisance due to their unpleasant odor but are also considered to be harmful to health.

Therefore, there has been no lack of attempt, to suppress the emission of hydrogen sulfide and/or mercaptans from sulfur-containing organic compounds with a high proportion of sulfur by means of adding appropriate additives to the sulfur-containing organic compounds or by treating the sulfur-containing organic compounds with appropriate compounds which are capable of inhibiting this type of emission.

For example, U.S. Pat. No. 4,778,609 describes sterically hindered imines which are able to inhibit the release of hydrogen sulfide from sulfur-containing lubricants. The disadvantage of these is that the imines used have to be considered to be a source of (form)aldehyde so that the release of (form)aldehyde has to be expected, which is regarded as a disadvantage from a health and ecological point of view.

U.S. Pat. No. 4,873,006 describes a method which is intended to inhibit the release of hydrogen sulfide from organic compounds with an active sulfur content in which these sulfur-containing compounds are treated with the reaction products of long-chain substituted polycarboxylic acids and hydroxylalkyl(poly)amines, optionally in the presence of alkali or alkaline earth metal-containing compounds. The disadvantage of this method is in particular the use of these types of metal containing compounds, which is now considered to be undesirable for ecological reasons. In addition, the reaction products of polycarboxylic acids and hydroxylamines used to treat the sulfur-containing compounds are complicated to prepare and to build up, which makes the process not very economically viable.

Furthermore, it is known, from Ullmann's Encyclopedia of Industrial Chemistry, Vol. A26, page 775, Fifth Completely Revised Edition 1995, VCH, Verlagsgesellschaft, ISBN 3-527-20126-2 and Houben-Weyl, Methoden der organischen Chemie, vol. E11/part 1 page 136 et seq., Georg Thieme Verlag Stuttgart, 1985, that hydrogen sulfide and mercaptans can be oxidized, and thus, made harmless, by their reaction with hydrogen peroxide. The main disadvantage of this method is that it is a two-phase reaction which requires increased technical costs and makes this method not very economically viable. Furthermore, it is not possible to oxidize all sulfur-containing, organic compounds with hydrogen peroxide, since some mercaptans, e.g. those based on α-olefins, cannot be oxidized in this way, or only very incompletely. In addition, very volatile undesirable secondary products are produced by superoxidation, which has a negative effect on the solubility behaviour of the organic sulfur-carrier. Over and above this, treatment with hydrogen peroxide, in particular, if it has to be repeated several times, has a quality impairing effect on the sulfur-carrier, e.g. the color deepens.

SUMMARY OF THE INVENTION

The object of the present invention is to provide a simple process for inhibiting the emission of hydrogen sulfide and/or mercaptans, if possible from all types of organic sulfur-carriers, which takes place without the use of additional metal compounds, without the release of (form) aldehyde and with a minimum of unwanted secondary reactions.

It has now been found that the use of organic hydroperoxides can stabilize organic, sulfur-containing compounds with a high proportion of sulfur, regardless of what raw materials (synthetic or natural) have been used as the basis for preparing these sulfur-containing compounds.

The present invention therefore provides a process for inhibiting the emission of hydrogen sulfide and/or mercaptans from sulfurized organic compounds with a high proportion of sulfur which is characterized in that the sulfurized organic compounds are treated with 0.01 to 10 wt. % of an organic hydroperoxide.

DETAILED DESCRIPTION OF THE INVENTION

The sulfurized organic compounds are preferably treated with 0.05 to 5, in particular 0.1 to 1.0 wt. %, with respect to the entire reaction mixture, of an organic hydroperoxide.

Suitable organic hydroperoxides which may be used for the process according to the present invention are, for example, tert.-butyl hydroperoxide, tert.-amyl hydroperoxide, cumene hydroperoxide and diisopropylbenzene monohydroperoxide. Obviously, it is also possible to use different organic hydroperoxides from those mentioned. Cumene hydroperoxide is preferably used, preferably in the form of its 10 to 90 wt. % strength solution, more preferably, its 70 to 80 wt. % solution, in cumene. Obviously, the other organic hydroperoxides may also be used in solution. Any inert organic solvents are suitable for this purpose.

Treatment of the sulfurized organic compounds with the organic hydroperoxides, which may be used individually or as a mixture with each other, generally takes place at reaction temperatures of about 0 to 150° C., preferably 30 to 120° C., in particular 50 to 80° C., wherein the decomposition point of the hydroperoxides being used restricts the upper temperature limit. The treatment time for sulfurized organic compounds with the hydroperoxides depends, inter alia, on the particular hydroperoxide being used and is about 1 to 120 minutes, preferably 5 to 60 minutes, more preferably, 15 to 45 minutes.

Suitable hydroperoxides are, in particular, those mentioned above by way of example which dissolve in the sulfurized organic compounds to be treated and the storage and handling of which is possible without too large a technical cost.

If the hydroperoxides are to be used in solution, if required, the organic solvent, for example cumene when using cumene hydroperoxide, can be removed by vacuum distillation after reaction is complete.

Obviously, it is possible to add other compounds known from the prior art, and which are capable of suppressing the emission of hydrogen sulfide and/or mercaptans, to the organic hydroperoxides. For example, hydrogen peroxide, sterically hindered imines or the reaction products of long-chain substituted polycarboxylic acids and hydroxylalkyl (poly)amines, optionally in the presence of alkali or alkaline earth metal-containing compounds.

Any sulfur-containing organic compounds with a high proportion of sulfur, generally more than 10 wt. %, which are used for example as EP additives in lubricants, can be treated using the process according to the present invention. These types of sulfur-containing organic compounds are prepared in a known way by the sulfurization of unsaturated organic compounds, wherein polysulfidic compounds with several sulfur atoms in the chain are obtained.

Suitable unsaturated organic compounds are those with one or more double bonds. The unsaturated organic compounds may be branched or unbranched, aliphatic, cycloaliphatic or aromatic hydrocarbons with 2 to 50 carbon atoms. Examples of such unsaturated organic compounds are isobutylene, propylene and their corresponding dimers, trimers or tetramers, polyisobutylene, 1-octene, 1-decene, 1-dodecene, $C_{20}$-$C_{24}$-poly-$\alpha$-olefins, cyclohexenes, dicyclopentadiene and octadecenol.

In addition, natural raw materials are also suitable as unsaturated organic compounds, such as animal or plant fats and oils. They contain mixtures of mono, di and triglycerides of saturated and unsaturated fatty acids. Unsaturated wax-esters are also included here. Examples of these types of raw materials are sunflower oil, rape seed oil, soy oil, peanut oil, castor oil, lard oil, tallow fat and fish oil. Obviously, the fats and oils mentioned may also be used in the form of the corresponding esters.

Sulfurization of unsaturated organic compounds is known and is generally performed with sulfur and/or hydrogen sulfide, with or without a catalyst, under normal or increased pressure at elevated temperature. After sulfurization of the organic compounds being used, nitrogen is blown through the reaction mixture to remove very volatile compounds and this is followed by an optional vacuum treatment in the form of a distillation or processing in a thin layer evaporator. This generally takes place at temperatures of about 50 to 150° C. and at a pressure of about 5 to 500 mbar.

In general, however, the post-treatment described for the sulfurized organic products is not sufficient to prepare sulfurized products from which the emission of hydrogen sulfide and/or mercaptans is no longer possible.

Using the process according to the present invention, however, sulfurized organic compounds with a high proportion of sulfur are obtained which exhibit virtually no emissions of hydrogen sulfide or mercaptans when they are used, for example, in lubricants as EP additives under high stress conditions (temperature and pressure).

EXAMPLES

The so-called hydrogen sulfide test described below is suitable for determining the unwanted emissions of hydrogen sulfide and/or mercaptans. This is carried out as follows:

15 g of the substance being tested are weighed into a 100 ml wide-necked bottle. A strip of lead acetate paper is moistened with water (this increases the sensitivity of the test) and is creased so that it can be clamped between the lid and the glass thread on the bottle. About ⅔ of this strip must hang freely in the space inside the bottle, over the substance being tested. The lead acetate paper must not come into contact with the substance. The bottle is firmly sealed and left for 30 minutes in a drying cabinet at 100° C. After cooling, the discoloration of the lead acetate paper is assessed. (The paper is colored black by $H_2S$ and brown by mercaptans).

Assessment makes use of the following visual scale:

score 1: no discoloration
score 2: slight brown coloration
score 3: brown coloration
score 4: black coloration Example 1

Sulfur carrier based on decene-1, sulfur content about 20%

The very volatile constituents were first removed, in a thin layer evaporator at about 120° C. and 20 mbar, from a crude sulfur carrier prepared from decene-1 using sulfur and hydrogen sulfide; $H_2S$ test: 4.

After cooling to 50° C., 1.0 wt. % of cumene hydroperoxide solution (80% strength in cumene) was added and the mixture was stirred for a further 1 hour; $H_2S$ test: 1.

Example 2

Sulfur carrier based on decene-1, sulfur content about 28%

The very volatile constituents were first removed, in a thin layer evaporator at about 120° C. and 20 mbar, from a crude sulfur carrier prepared from decene-1 using sulfur and hydrogen sulfide; $H_2S$ test: 4.

After cooling to 60° C., 0.25 wt. % of cumene hydroperoxide solution (80% strength in cumene) was added and the mixture was stirred for a further ½ hour; $H_2S$ test: 1.

Example 3

Sulfur carrier based on rape seed oil and the methyl ester of rape seed oil, sulfur content about 10 %

A crude sulfur carrier prepared from rape seed oil and the methyl ester of rape seed oil using sulfur and hydrogen sulfide was first distilled for 2 hours at 100° C. and 20 mbar; $H_2S$ test: 4.

After cooling to 50° C., 1.0 wt. % of cumene hydroperoxide solution (80% strength in cumene) was added and the mixture was stirred for a further I hour; $H_2S$ test: 1.

Example 4

Sulfur carrier based on rape seed oil and the methyl ester of rape seed oil and decene-1, sulfur content about 15%

A crude sulfur carrier prepared from rape seed oil and the methyl ester of rape seed oil and decene-1 using sulfur and hydrogen sulfide was first distilled for 2 hours at 100° C. and 20 mbar; $H_2S$ test: 4.

After cooling to 50° C., 0.5 wt. % of cumene hydroperoxide solution (80% strength in cumene) was added and the mixture was stirred for a further 1 hour; $H_2S$ test: 1

Example 5

Sulfur carrier based on sunflower oil and the methyl ester of rape seed oil, sulfur content about 15%

A crude sulfur carrier prepared from sunflower oil and the methyl ester of rape seed oil using sulfur and hydrogen sulfide was treated, without a distillation stage, with 0.5 wt. % of cumene hydroperoxide solution (80% strength in cumene) and the mixture was stirred for a further ½ hour; $H_2S$ test: 1.

Although the invention has been described in detail in the foregoing for the purpose of illustration, it is to be understood that such detail is solely for that purpose and that variations can be made therein by those skilled in the art without departing from the spirit and scope of the invention except as it may be limited by the claims.

What is claimed is:

1. A process for inhibiting the emission of hydrogen sulfide and/or mercaptans from sulfurized organic compounds with a high sulfur content, wherein the sulfurized organic compounds are treated with 0.01 to 10 wt. %, with respect to the entire reaction mixture, of an organic hydroperoxide.

2. A process according to claim 1, wherein the organic hydroperoxide is selected from the group consisting of tert.-butyl hydroperoxide, tert.-amyl hydroperoxide, cumene hydroperoxide and/or diisopropylbenzene monohydroperoxide.

3. A process according to claim 1, wherein cumene hydroperoxide is used in the form of its 10 to 90 wt. % strength solution in cumene.

* * * * *